United States Patent
Capasso et al.

(10) Patent No.: US 6,760,354 B2
(45) Date of Patent: Jul. 6, 2004

(54) INTERSUBBAND LIGHT EMITTERS WITH INJECTION/RELAXATION REGIONS DOPED TO DIFFERENT LEVELS

(75) Inventors: Federico Capasso, Westfield, NJ (US); Alfred Yi Cho, Summit, NJ (US); Rafaelle Colombelli, Hoboken, NJ (US); Claire F. Gmachl, New Providence, NJ (US); Trinesha Shenika Mosely, Gibson, LA (US); Axel Straub, Kingsford (AU); Deborah Lee Sivco, Warren, NJ (US); Mariano Troccoli, Chatham, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 149 days.

(21) Appl. No.: 10/096,702

(22) Filed: Mar. 12, 2002

(65) Prior Publication Data

US 2003/0174749 A1 Sep. 18, 2003

(51) Int. Cl.[7] .................................................. H01S 5/32
(52) U.S. Cl. ........................................................ 372/45
(58) Field of Search .............................................. 372/45

(56) References Cited

U.S. PATENT DOCUMENTS 6,476,411 B1 * 11/2002 Ohno et al. ................... 257/15

OTHER PUBLICATIONS

US 6,344,199, 11/2001, Capasso et al. (withdrawn)*
R. F. Kazarinov et al., *Possibility of the Amplification . . .*, Sov. Phys. Semic., vol. 5, No. 4, p. 707 (Oct. 1971).
J. Faist et al., *Quantum Cascade Laser*, Science, vol. 264, p. 553 (Apr. 1994).
C. Gmachl et al., *Quantum cascade lasers with a heterogenous cascade . . .*, Appl. Phys. Lett., Vo. 79, No. 5, p. 572 (Jul. 2001).

* cited by examiner

Primary Examiner—James W. Davie

(57) ABSTRACT

In an intersubband light emitter, at least two injection/relaxation (I/R) regions contiguous with the same RT region have different doping levels. Preferably, one I/R region has a doping level that is at least 100 times lower than that of the other I/R region. In one embodiment, one I/R region is undoped, whereas the other I/R region is doped.

15 Claims, 4 Drawing Sheets

INTERSUBBAND LIGHT EMITTERS WITH INJECTION/RELAXATION REGIONS DOPED TO DIFFERENT LEVELS

GOVERNMENT CONTRACT

This invention was made with Government support under Contract No. DAAD19-00-C-0096 by the DARPA/US Army Research Office. The Government has certain rights in this invention.

BACKGROUND OF THE INVENTION

1. Field of the Invention

This invention relates to intersubband (ISB) semiconductor light emitters in general and to quantum cascade (QC) semiconductor lasers in particular.

2. Discussion of the Related Art

In the relatively short period of only eight years since ISB light emitters, especially lasers, were first reported in the literature, they have already reached a high level of maturity, which is amply demonstrated by their technological performance and their frequent use in various demanding applications, mostly in trace gas sensing in the mid-infrared wavelength range.

A conventional ISB laser includes a semiconductor waveguide with an active core comprising a stack of alternating unipolar radiative transition (RT) regions and injection/relaxation (I/R) regions. In the RT regions light is generated by electrons undergoing optical, intersubband transitions in coupled quantum wells or short period superlattices. The I/R regions provide electron transport between successive RT regions. While it is customary that all RT regions are essentially identical to one another, and that likewise all I/R regions are essentially identical to one another, it has recently been shown—by using two different, stacked cascades in one waveguide core—that this is not an essential requirement. [See, C. Gmachl et al., *Appl. Phys. Lett.* Vol. 79, No.5, pp. 572 (2001), which is incorporated herein by reference.]

Another commonly held principle in ISB technology is that the I/R regions must be doped. In fact, early proposals of ISB injection lasers [e.g., R. F. Kazarinov et al., *Sov. Phys. Semicond.*, Vol. 5, No. 4, p. 207 (1971)] did not include I/R regions and hence could not incorporate extrinsic carriers in the I/R regions. By extrinsic we mean carriers intentionally added to a region of the device by doping. Experiments on such devices failed to produce lasing action. The failure was due primarily to space charge injection, which did not allow the applied electric field to be uniform across the structure. In contrast, the first demonstration of a QC-laser included both I/R regions and extrinsic carriers (e.g., electrons) in the I/R regions. [See, J. Faist et al., *Science*, Vol. 264, p. 553 (1994), which is incorporated herein by reference.] However, even in the early stages of that work it was understood that—while dopants were seemingly necessary—they did negatively affect some aspects of laser action. First, impurity scattering considerably broadens the gain spectrum, thereby increasing the threshold current density. Second, impurity scattering shortens the non-radiative scattering time of the upper laser level, thus reducing the population inversion. Third, free carrier absorption by the extrinsic carriers increases the waveguide loss in a region of the waveguide with maximum optical intensity, again raising the laser threshold.

BRIEF SUMMARY OF THE INVENTION

We have discovered that doping all of the I/R regions of an ISB light emitter is not an essential requirement for lasing action. In addition, we have found that the overall performance of an ISB laser is enhanced by making the doping levels different in at least two I/R regions that are contiguous with the same RT region. Preferably, the two I/R regions have doping levels that are at least 100 times different from one another. In one embodiment, one I/R region is undoped, whereas the other I/R region is doped. By undoped we mean that the region in question is not intentionally doped; that is, any doping of such a region or layer is relatively low and typically results from residual or background doping in the chamber used to grow the layers of the device.

BRIEF DESCRIPTION OF THE SEVERAL VIEWS OF THE DRAWING

Our invention, together with its various features and advantages, can be readily understood from the following more detailed description taken in conjunction with the accompanying drawing, in which.

3.6/2.7/1.2/7.8/1.0/6.1/2.8/4.8/1.9/<u>3.4</u>/<u>1.9</u>/<u>3.2</u>/1.8/2.9/1.7/ 2.6/3.8/2.3/ 1.2/6.5/1.2/5.3/2.1/4.8/1.8/<u>3.7</u>/<u>1.3</u>/<u>3.8</u>/1.0/ 3.1/0.9/3.3.

Figure 5:
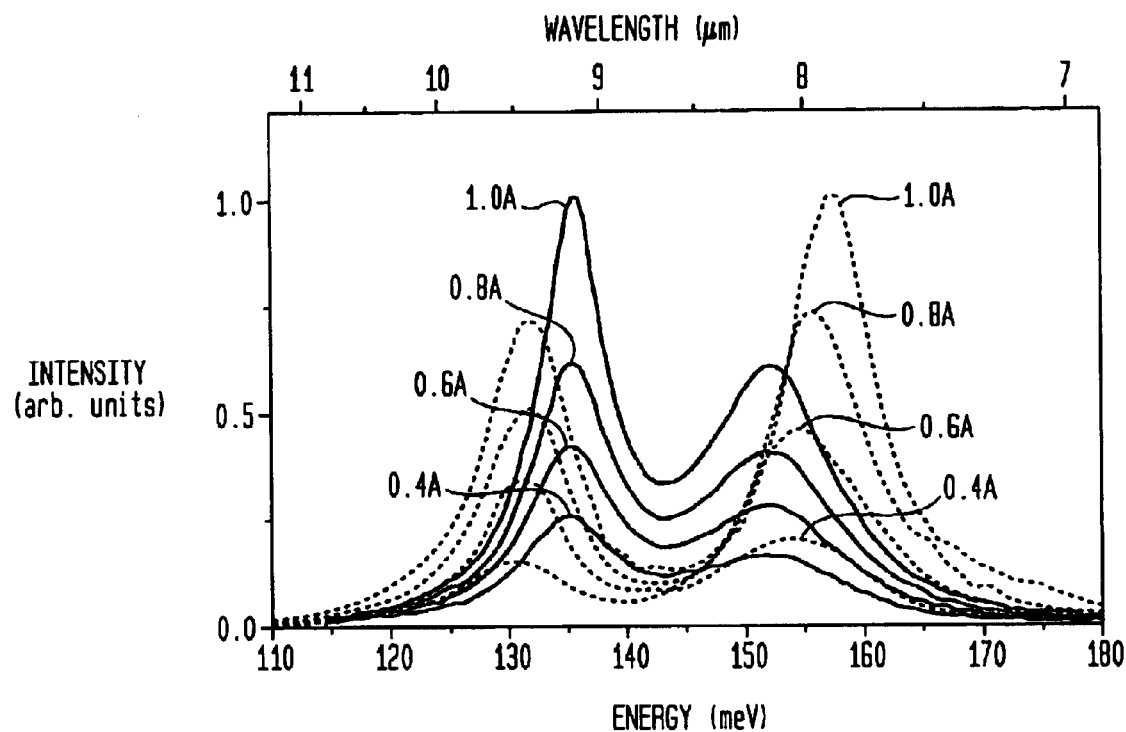
Figure 8:
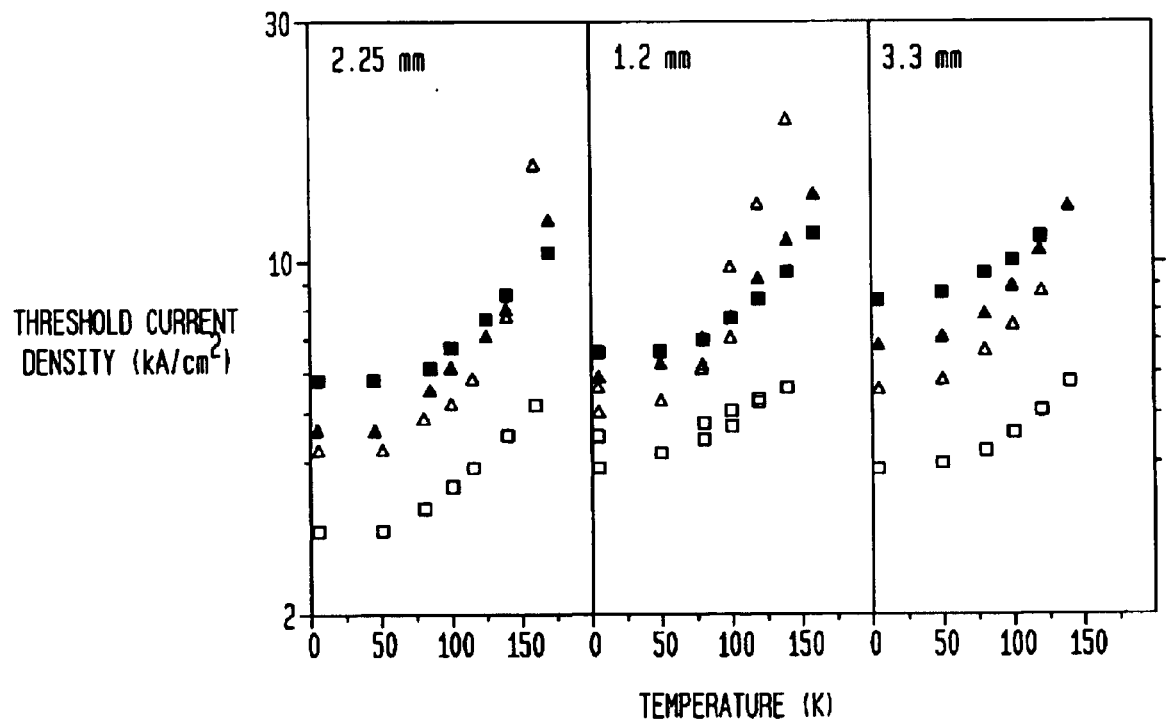
Figure 6:
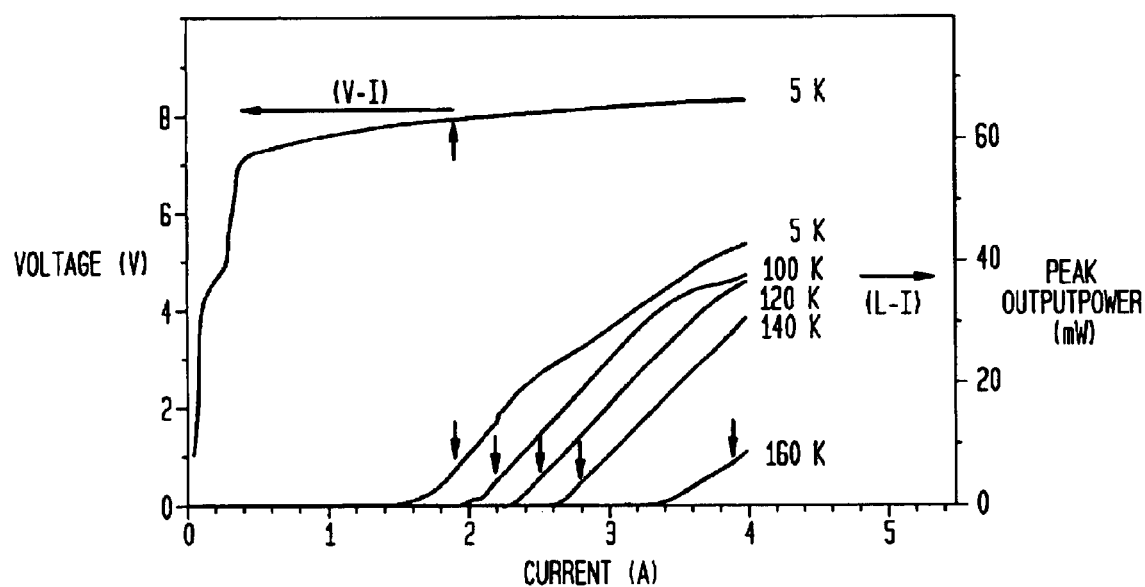
Figure 7:
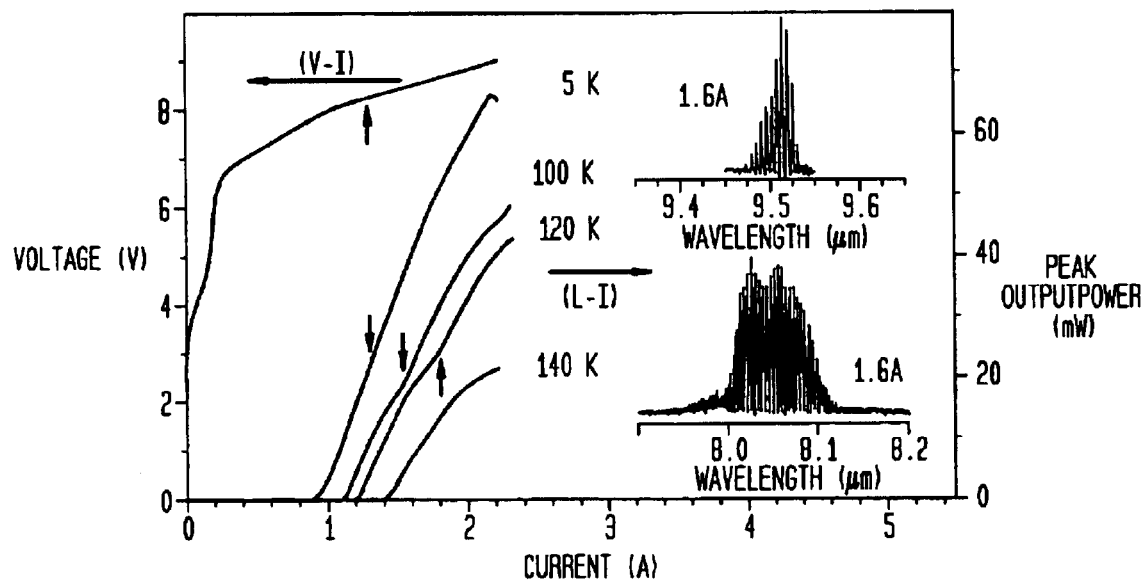

The first RT region begins at the 3.6 nm layer and ends at the 2.8 nm layer; the first I/R region begins at the immediately adjacent 4.8 nm layer and ends at the 2.6 m layer; the second RT region begins at the immediately adjacent 3.8 nm layer and ends at the 2.1 nm layer; and the second I/R region begins at the immediately adjacent 4.8 nm layer and ends at the 3.3 nm layer. The underlined layers are Si-doped in both samples to a density of n=4×10$^{17}$ cm$^{-3}$. In the reference sample the dotted underlined layers are also Si-doped to a density of n=4×10$^{17}$ cm$^{-3}$. The experimentally obtained peak wavelengths of 8.0 and 9.5 $\mu$m are in reasonable agreement with the design wavelengths of 8.4 and 9.8 $\mu$m, respectively;

FIG. 5 shows electro-luminescence spectra of deep-etched, semi-circular mesas operated in a pulsed, spontaneous emission mode at a 10 K heat sink temperature and various peak current levels. The dashed lines indicate ISB emitters that have some undoped I/R regions in accordance with one embodiment of our invention. (Hereinafter, these devices will be referred to as being partially undoped.) The solid lines indicate conventional ISB emitters in which all I/R regions are essentially identically doped. The corresponding current densities are 2.5, 3.8, 5.1 and 6.4 kAcm$^{-2}$;

FIGS. 6–7 show light output (L) and voltage (V) versus current (I) characteristics of deep-etched, ridge waveguide lasers operated in a pulsed mode at various heat sink temperatures. FIG. 6 shows L-I-V characteristics of a reference laser (14 μm wide and 2.25 mm long). In the reference laser the 9.5 μm emission lased first, and the small, vertical arrows indicate the thresholds of the 8.0 μm emission. In contrast, FIG. 7 shows L-I-V characteristics of a partially undoped laser (14 μm wide and 2.22 mm long) in accordance with one embodiment of our invention. In this embodiment the 8.0 μm emission lased first, and the arrows indicate the thresholds of the 9.5 μm emission. Both types of lasers were operated with 50-ns-long current pulses at an 84.2 kHz repetition rate. The insets of FIG. 7 show spectra of the partially undoped laser operated at a pump current of 1.6 A;

FIG. 8 shows a comparison of the threshold current densities of the two different samples at the two different wavelengths. For lasers of various lengths as indicated, the threshold current densities were measured versus heat sink temperature. Squares show the threshold current densities of the 8.0 μm radiation, and triangles indicate 9.5 μm emission, with the conventionally doped sample being represented by the filled symbols, and the partially undoped sample by the open symbols. The strong reduction in laser threshold for the QC-laser RT regions preceded by the undoped I/R region (8.0 μm, ■→□) can clearly be seen and compared to the minor reduction for the conventionally doped QC-laser (9.5 μm, ▲→△). The temperature behavior of the lasers can be understood from thermal back-filling.

In the interest of clarity and simplicity, FIGS. 1–4 have not been drawn to scale. In addition, when describing physical or optical dimensions, the symbol A stands for Angstroms, whereas when describing electric current, it stands for Amperes.

DETAILED DESCRIPTION OF THE INVENTION

General Structure of Homogeneous and Heterogeneous ISB Devices

Figure 1:
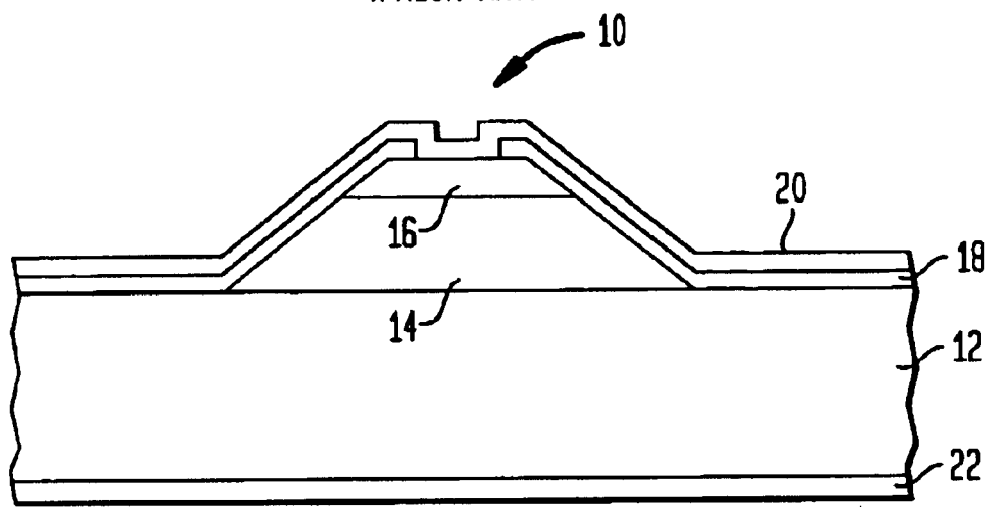
FIG. 1 is a schematic, cross sectional view of a prior art ISB light emitter with homogeneous cascades.

Before discussing our invention in detail, we first turn to to FIG. 1, which shows a prior art homogeneous ISB semiconductor light emitter (e.g., a QC laser) 10 comprising a core region 14 sandwiched between an upper cladding region 16 and a lower cladding region 12. The core region includes the active region of the laser. The active region, in turn, includes a multiplicity of essentially identical repeat units or stages; that is, the overall device is termed homogeneous. In a typical design, each stage includes a radiative transition (RT) region and an adjacent injection/relaxation (I/R) region. All stages are essentially identical to one another.

The term ISB in general refers to the well-known unipolar nature of the optical and electronic transitions that take place in the RT and I/R regions.

Typically the substrate on which the various layers of the emitter are formed serves as the lower cladding region. Alternatively, a lower cladding region, separate from the substrate, may be formed between the substrate and the core region. The upper cladding region 16 and the core region 14 are illustratively formed in the shape of a mesa or trapezoid typical of ridge waveguide laser structures. The mesa may be deep-etched as shown to stop at or near the bottom of the core region 14, or it may be shallow-etched (not shown) so that the mesa extends only through the upper cladding region.

In either case, an electrically insulating layer 18 (e.g., $Si_3N_4$ or $SiO_2$) is formed over the top of the device and is patterned to form an opening that exposes a portion of the top of the mesa. Alternatively, the insulating layer may comprise a chalcogenide glass of the type described by J. N. Baillargeon et al. in copending U.S. patent application Ser. No. 09/611,886 filed on Jul. 7, 2000, now U.S. Pat. No. 6,463,088, which issued on Oct. 8, 2002 is assigned to the assignee hereof, and is incorporated herein by reference. A first electrode 20 is formed over the insulating layer 18 and in the opening so as to contact the upper cladding region (usually by means of a highly doped contact-facilitating layer, not shown), and a second electrode 22 is formed on the substrate 12.

The substrate itself may be a single crystal semiconductor body or a combination of such a body with another layer (e.g., an epitaxial layer grown on the top surface of the body). Illustratively, lasers of this type are fabricated from Group III–V compound semiconductors; e.g., In-based Group III–V compounds such as GaInAs and AlInAs for operation at mid-infrared wavelengths of about 4–24 μm. At shorter wavelengths, Group III–V compounds such as GaN and AlGaN may be used. Within any particular materials system the specific wavelength of operation is determined primarily by the thickness of the quantum wells that make up the RT regions.

Drive circuitry, not shown, is coupled across the electrodes in order to provide an external voltage bias and to supply pumping energy (e.g., electric current) to the laser of sufficient magnitude to generate light. Below threshold the emitter operates as an incoherent, spontaneous emission source, whereas above threshold it operates as a coherent, stimulated emission source. In the latter case, when provided with optical feedback, the source functions as a laser. Suitable optical feedback is typically provided by an optical cavity resonator formed, for example, by cleaved crystal facets, distributed feedback (DFB) gratings, distributed Bragg reflectors (DBRs), or a combination of them. In FIG. 1 one cleaved facet of the resonator might be the end face depicted, whereas the other, parallel facet would be at the opposite end (not shown) of the laser.

Figure 2:
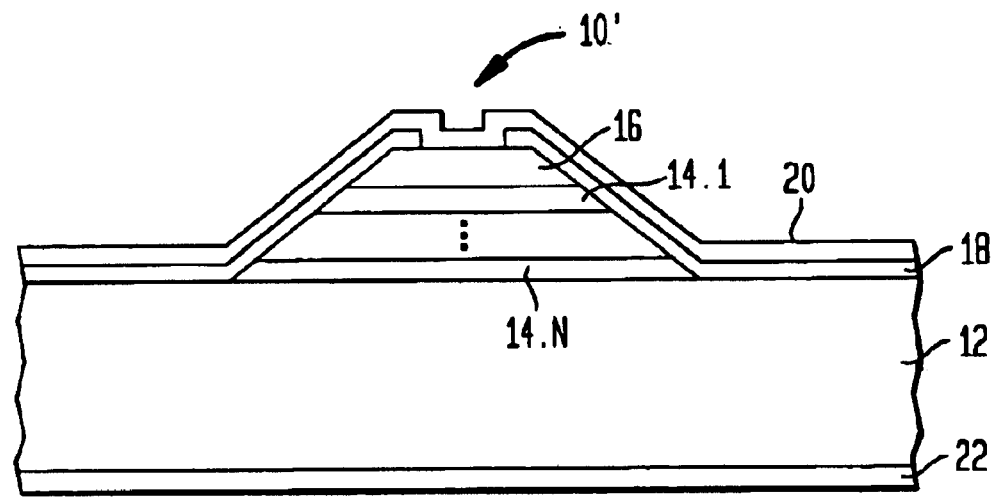
FIG. 2 is a schematic, cross sectional view of a prior art ISB light emitter with heterogeneous cascades.

In contrast with a homogeneous ISB light emitter, a heterogeneous ISB (HISB) light emitter includes a stack of at least two different ISB sub-emitters. This type of HISB device is heterogeneous in that at least one sub-emitter is designed to emit light at a center wavelength that is different from that of at least one other sub-emitter. HISB devices in general, and HISB light emitters in particular, are described by C. Gmachl et al., supra, and F. Capasso et al., copending U.S. patent application Ser. No. 09/883,542 filed on Jun. 18, 2001 which is assigned to the assignee hereof and is incorporated herein by reference. In FIG. 2 we illustrate one embodiment of a HISB device 10' that is similar to the homogeneous device of FIG. 1 except that the core region includes a multiplicity of N stacked active regions 14.1–.N at least two of which are designed to emit light at different center wavelengths (e.g., at 8.4 μm and 9.8 μm). Each active region is a separate ISB sub-device that includes an RT region and an adjacent I/R region. Because the ISB sub-devices are unipolar, the order in which they are stacked can be chosen at will.

We note here that the Gmachl paper, supra, describes an HISB laser that includes two stacks: a bottom stack that emits at 8.0 μm and has a multiplicity of I/R regions each doped to a sheet density of $2.4 \times 10^{11}$ cm$^{-2}$ and a top stack that emits at 5.2 μm and has a multiplicity of I/R regions each doped to a sheet density of $3.1 \times 10^{11}$ cm$^{-2}$. However, this device does not include a pair of differently-doped I/R regions contiguous with the same RT region, does not describe I/R regions having doping levels that are at least 100 times different from one another, and does not achieve the threshold reduction demonstrated by our invention.

Partially Undoped Injection/Relaxation Regions

Figure 3:
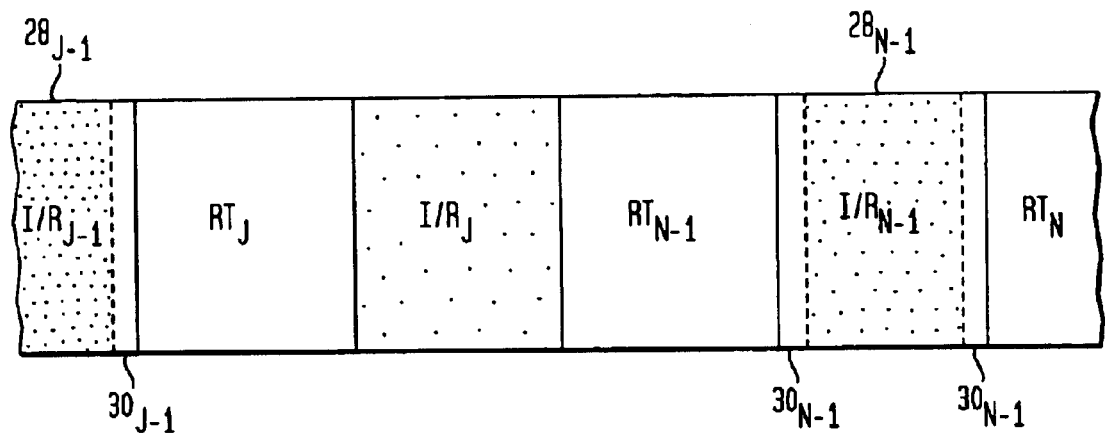
FIG. 3 is a schematic view of the repeat units of an ISB light emitter in accordance with one embodiment of our invention.

In accordance with one aspect of our invention, the overall performance of an ISB emitter is enhanced (e.g., threshold of an ISB laser is reduced) by making the doping levels different in at least two I/R regions contiguous with the same RT region. In particular, as shown in FIG. 3, at least one I/R region (e.g., I/R$_j$) has a doping level that is different from that of another I/R region (e.g., I/R$_{j-1}$), and the two I/R regions are contiguous with the same RT region (e.g., RT$_j$). Preferably, the I/R$_j$ region has a doping level that is at least 100 times lower than that of the I/R$_{j-1}$ region. (Hence, region I/R$_j$ is depicted with a lower density of dots than region I/R$_{j-1}$.) In one embodiment, the region I/R$_j$ is undoped, whereas the regions I/R$_{j-1}$ are intentionally doped. A similar exposition applies to the I/R regions I/R$_j$ and I/R$_{n-1}$, which are contiguous with the same RT region (RT$_{n-}$) For example, in the InGaAs/AlInAs materials system using Si as the dopant, the undoped I/R regions would typically have a dopant concentration of less than about $10^{15}$ cm$^{-3}$ (sometimes referred to as an intrinsic semiconductor since the Fermi level would be located in the bandgap), whereas the doped I/R regions would typically have a dopant concentration of greater than about $10^{15}$ cm$^{-3}$.

In practice, however, it is the amount of charge (e.g., electrons) present in the I/R regions that matters, rather than the distribution of dopants in the I/R regions. Therefore, the sheet density of the I/R regions is a better parameter by which to design ISB or HISB light emitters in accordance with our invention. In this regard, we prefer the sheet density of the undoped I/R regions to be about $10^8$–$10^9$ cm$^{-2}$, whereas the sheet density of the doped I/R regions should be about $10^{11}$–$10^{12}$ cm$^{-2}$. Below about $10^{11}$ cm$^{-2}$ there is insufficient charge in the I/R regions to prevent "break up" of the conduction band structure under an applied electric field, and above about $10^{12}$ cm$^{-2}$ optical losses (e.g., free carrier absorption) may be too high. In addition, the appropriate sheet density is wavelength dependent, with longer wavelength emitters usually requiring lower sheet densities.

When intentionally doping an I/R region, it is not essential, nor even desirable in all cases, that the entirety of the region be doped. In fact, we prefer that only a central section (28, FIG. 3) of the I/R regions be doped, leaving undoped buffer regions 30 on either side to separate the ionized dopant atoms in the central section from the adjacent RT regions. The width of the buffer regions is preferably greater than the larger of the scattering length and the diffusion length of the ionized dopant atoms.

FIG. 3 suggests, but does not require, that the higher doped and lower doped (e.g., undoped) I/R regions alternate with one another, with adjacent pairs of I/R regions being separated by an RT region. However, other sequences of doped and undoped I/R regions are possible and may even be desirable; e.g., it may be advantageous to utilize a periodic sequence in which each period comprises two undoped I/R regions followed by a doped I/R region, with each adjacent pair of I/R regions again being separated by an RT region.

EXAMPLE

This example describes a Group III–V compound semiconductor, dual-wavelength HISB laser that was designed for operation at center wavelengths of 8.4 μm and 9.8 μm. An undoped I/R region preceded each 8.4 μm RT region, whereas a doped I/R region preceded each 9.8 μm RT region, in accordance with one embodiment of our invention. Various materials, dimensions and operating conditions are provided by way of illustration only and, unless otherwise expressly stated, are not intended to limit the scope of the invention.

Figure 4:
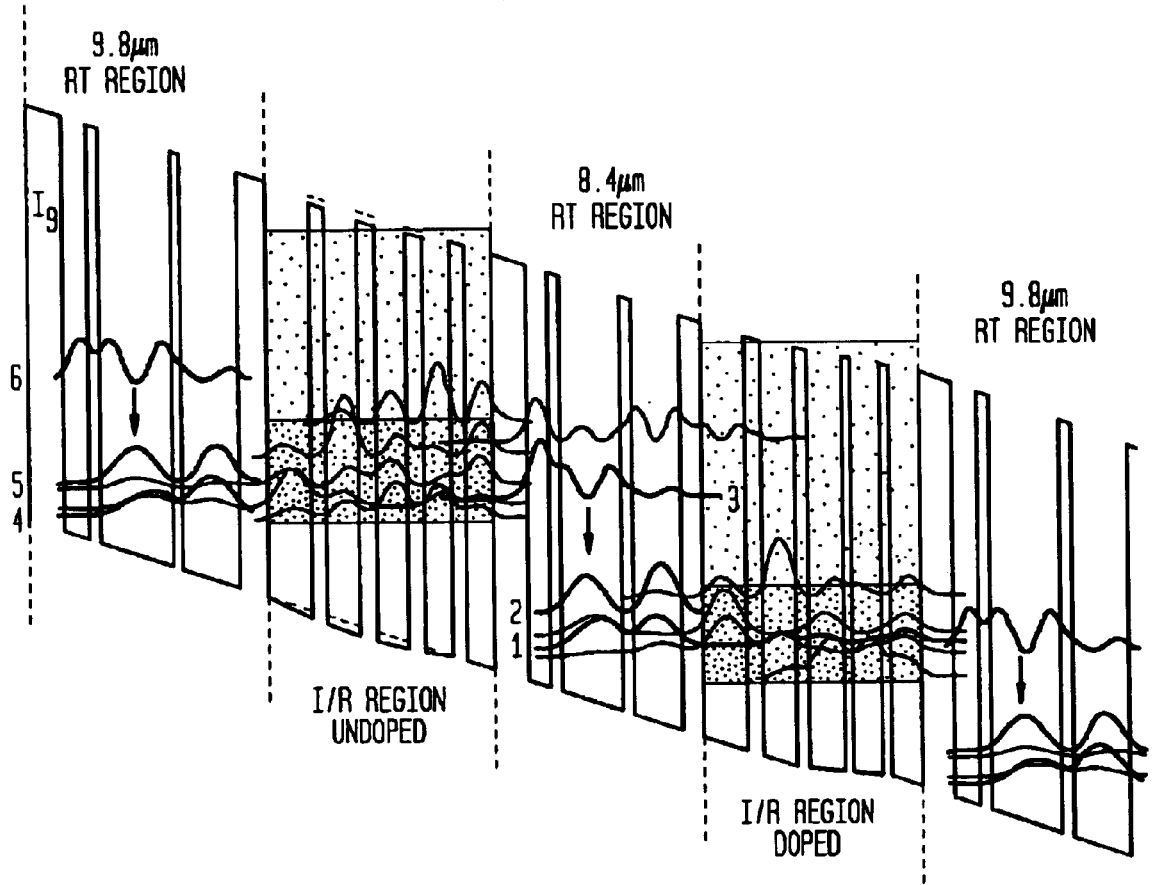
FIG. 4 shows the conduction band diagram and the moduli squared of the electron wavefunctions of three RT regions with interleaved I/R regions calculated using iteratively Schroedinger's and Poisson's equations under an applied external electric field of 37 kV/cm. The dotted line indicates the correction to the band diagram if the I/R region preceding the 8.4 $\mu$m RT region is undoped. The thick lines represent the moduli squared of the wavefunctions involved in the laser transitions (labeled "1", "2", "3" for the 8.4 $\mu$m RT region and "4", "5", "6" for the 9.8 $\mu$m RT region, respectively). The arrows indicate the laser transitions. The nominal layer thicknesses in nanometers of one period from left to right starting from the first injection-barrier ($I_9$) are.

More specifically, the HISB laser of this example was a dual-wavelength, interdigitated cascade, QC laser; i.e. the laser had a first stack of RT and I/R regions designed for emission at one center wavelength (8.4 μm) interleaved with a second stack designed for emission at a substantially different center wavelength (9.8 μm). In practice, the RT regions actually emitted at two different wavelengths (8.0 and 9.5 μm, respectively) that were slightly different from the design wavelengths. As shown in FIG. 4, which represents only a portion of a much longer structure, the I/R regions bridged the 8.4 μm RT regions and the 9.8 μm RT regions to one another. Importantly, in the sample designed in accordance with one embodiment of our invention, the I/R regions that immediately preceded the 8.4 μm RT regions were undoped, whereas the central sections of the I/R regions that immediately preceded the 9.8 μM RT regions were doped with Si. For purposes of comparison, in a reference sample that was otherwise identical to the invention sample, the central sections of all I/R regions were doped with Si.

We observed two-wavelength laser action for both samples, which clearly demonstrates that, contrary to conventional wisdom, it is not an essential requirement for QC-lasers that all I/R regions be doped. Moreover, the overall performance of the invention sample was greatly improved, showing a reduction in threshold by a factor of ~2 compared to the same-wavelength laser with doped I/R regions. The dual-wavelength characteristic of this QC-laser allowed a straightforward evaluation of the doped (represented by one wavelength) versus undoped (represented by the other wavelength) I/R regions. (However, we expect the threshold reduction observed in these HISB devices to also be realized in homogeneous ISB lasers in which selected I/R regions are undoped.)

The samples were grown by molecular beam epitaxy (MBE) in the InGaAs/AlInAs materials system and were lattice matched to a low-doped (n≈2×10$^{17}$ cm$^{-3}$) InP substrate 12 (FIG. 2). For both structures a 650 nm thick low-doped (n≈5×10$^{16}$ cm$^{-3}$) InGaAs buffer layer was first grown on the InP-substrate, which simultaneously served as the bottom cladding region. The waveguide core comprised a stack containing N$_p$=20 repeat units (RUs). Each RU contained two different RT regions of the well-known three-well-vertical-transition type. One RT region emitted at a center wavelength of 8.0 μm, the other at 9.5 μm. These RT regions were interleaved with corresponding I/R regions as described above. The choice of the RT regions was guided by their uncomplicated energy level structure.

The overall stack had a thickness of about 1.91 μm. In both structures each I/R region immediately preceding a 9.5 μm RT region was doped in its center portion to a sheet density of about 3.52×10$^{11}$ cm$^{-2}$, which is approximately twice the usual value in conventional ISB lasers using a similar design for operation at a comparable wavelength and was chosen to accentuate effects related to doped and undoped I/R regions. In the reference sample each I/R region immediately preceding a 8.0 μm RT region was also doped to a sheet density of about 3.4×10$^{11}$ cm$^{-2}$; the corresponding I/R regions in the invention sample were undoped.

The waveguide core was capped by 400 nm of low-doped InGaAs (n≈5×10$^{16}$ cm$^{-3}$), 2.9 μm of low-doped AlInAs (2.1 μm at n≈1×10$^{17}$ cm$^{-3}$ followed by 800 nm at n≈2×10$^{17}$ cm$^{-3}$), and 1 μm of high-doped (n 4×10$^{18}$ cm$^{-3}$) InGaAs. For the partially undoped, invention sample (subscript u=undoped) we estimated waveguide losses $\alpha_{w8,u}$ and $\alpha_{w9,u}$ to be 21.5 and 21.7 cm$^{-1}$, for 8.0 and 9.5 μm wavelengths, respectively. The corresponding, estimated waveguide losses of the fully doped reference sample (subscript d=doped) were $\alpha_{w8,d}=26.9$ cm$^{-1}$ and $\alpha_{w9,d}=31.4$ cm$^{-1}$, clearly larger than those of the invention sample owing to increased free carrier absorption. Confinement factors $\Gamma_{8,u,d}$ and $\Gamma_{9,u,d}$ for the respective RT regions were computed as 0.14 and 0.15, respectively, and were independent of the doping scheme. The effective refractive indices were calculated as $n_{eff,8,d} \approx 3.29$, $n_{eff,8,u} \approx 3.30$, and $n_{eff,9,d} \approx n_{eff,9,u} \approx 3.28$.

FIG. 4 shows the conduction band diagram of a RU with doped and undoped I/R regions calculated at the experimentally determined threshold electric field of 37 kV/cm. As can be seen, the difference in doping scheme does not significantly affect the band structure. The optical dipole matrix elements $z_{32,d}$ and $z_{32,u}$ for the 8.0 μm laser transition (between energy level "3" and "2") of the reference sample and the invention sample were calculated as $z_{32,d} \ z_{32,u}$ 2.0 nm. For the 9.5 μm laser transition ("6"→"5") they were computed as $z_{65,d} \ z_{65,u}$ 2.6 nm, respectively. Moreover the electron scattering times $\tau_{32,u} \approx \tau_{32,d}$ and $\tau_{65,u} \approx \tau_{65,d}$ as a result of longitudinal optical (LO) phonon emission were calculated as 3.27 ps and 2.05 ps, respectively. The scattering lifetimes ($\tau_{2,u}$, $\tau_{5,u}$, $\tau_{2,d}$, and $\tau_{5,d}$) for electrons in the lower laser level were all calculated as ≈0.3 ps. The design energies of the optical transitions, $E_{32,u,d}$ (=148 meV≡8.4 μm) and $E_{65,u,d}$ (=127 meV≡9.8 μm), were in reasonable agreement with the measured values (8.0 and 9.5 μm), allowing for some systematic deviations in layer thicknesses between the designed and actually grown sample.

FIG. 5 shows a comparison of the luminescence spectra obtained at various current levels for the two samples measured from deep-etched, round mesas (spontaneous emission devices, not lasers) cleaved along the diameter, and with the light collected from the resulting cleaved facet. The sets of spectra were normalized to the maximum intensity at a peak current level of 1 A. The small shifts of the peak wavelengths can be attributed to layer thickness variations. A clear difference in the overall shape of the spectra was observed between the two samples. While the reference sample (solid lines) displayed the larger intensity at ~9.5 μm, the stronger emission of the invention sample (dashed lines) was at the 8.0 μm transition. The electroluminescence power at each wavelength was approximately proportional to $E_{32(65)} \cdot (\tau_{3(6)}/\tau_{rad,32(65)}) \cdot N_p \cdot I \cdot \eta$, with $\tau_{3(6)}$ being the nonradiative scattering lifetime of the upper energy level, $\tau_{rad,32(65)}$ ($>>\tau_{3(6)}$) its radiative scattering time, I the current, and η the collection efficiency. Thus, the reversal of the relative emission strengths with wavelength (i.e., the higher intensity of the 8.0 μm optical transition for the invention sample) indicated a significantly increased internal quantum efficiency ($\tau_{3(6)}/\tau_{rad,32(65)}$) for the latter, resulting from an increased upper level scattering time, which is consistent with decreased impurity scattering. The full width at half maximum (FWHM) values were extracted from the luminescence measurements by fitting the sum of two Lorentzian lineshape functions to the data. The FWHM values $2\gamma_{32,u}$ and $2\gamma_{65,u}$ ($2\gamma_{32,d}$ and $2\gamma_{65,d}$) at a current level of 0.6 A were 9.5 meV and 7.9 meV (13.0 meV and 8.0 meV), respectively. Clearly the FWHM has been reduced for the RT regions preceded by the undoped I/R regions. Using the equations given by Faist et al, *Appl. Phys. Lett.*, Vol. 68, No. 26, p. 3680 (1996), which is incorporated herein by reference, and the experimentally obtained FWHM values, we calculated the gain coefficients for the various wavelength lasers under the two doping schemes as $g_{9,u} \approx g_{9,d} \approx 157$ cm/kA and $g_{8,u} \approx 143$ cm/kA and $g_{8,d} \approx 101$ cm/kA.

FIGS. 6–7 show the light output (L) and voltage (V) versus current (I) characteristics of two otherwise identical, doped and partially undoped QC-lasers operated in pulsed mode at various heat-sink temperatures. The processing of the devices and the measurement procedures were the same as described by Gmachl et al., supra. The fact that the partially undoped, invention sample displayed laser action at both wavelengths clearly demonstrates the efficacy of undoped I/R regions. Moreover, the slope efficiency of the invention sample increased to 60 mW/A with respect to the reference sample (25 mW/A), which can only partly be explained by the reduced free carrier absorption and therefore reduced waveguide losses. The inset of FIG. 7 also shows a laser spectrum displaying simultaneous two-wavelength emission and the typical Fabry-Perot modes of the as-cleaved laser.

FIG. 8 shows a comparison of the threshold current densities of the two samples and the two different wavelengths. Laser ridges with widths of 14 to 18 μm were cleaved to lengths of 1.2 mm, 2.25 mm and 3.2 mm, which resulted in mirror losses $\alpha_{m8,d} \ \alpha_{m9,d} \ \alpha_{m8,u} \ \alpha_{m9,u}$ of 10.4 cm$^{-1}$, 5.6 cm$^{-1}$, and 3.9 cm$^{-1}$, respectively. Since the two wavelengths could not easily be separated during the L-I-V characterization measurements, the threshold currents were read from the real-time spectral monitor of a Fourier Transform Infrared spectrometer. The low temperature behavior of the threshold current densities of the reference sample can be understood from the calculated values. Using the estimated waveguide and mirror losses and the calculated gain coefficients, we expected a lower threshold current density (1.6 kA/cm$^2$ for a 2.25 mm long device) for the 9.5 μm radiation than for the 8.0 μm radiation (2.3 kA/cm$^2$). This trend was well reproduced in the experimental data (4.6 kA/cm$^2$ at 9.5 μm, versus 5.8 kA/cm$^2$ at 8.0 μm), taking into account that the overall larger values are partially caused by additional waveguide losses from the side-wall coating.

For the invention sample—with its significantly larger gain for 8.0 μm radiation and the generally lower waveguide loss—we consequently expected a 45% reduction of the threshold current density for the 8.0 μm radiation and a 20% reduction for the 9.5 μm radiation, respectively, over the values obtained for the reference sample. In fact, we observed a large reduction (~47%) in the threshold current density of the 8 μm emission (to 3.07 kA/cm$^2$) and only a much smaller one (13%) for the 9 μm emission (to 4.0 kA/cm$^2$).

It is to be understood that the above-described arrangements are merely illustrative of the many possible specific embodiments that can be devised to represent application of the principles of the invention. Numerous and varied other arrangements can be devised in accordance with these principles by those skilled in the art without departing from the spirit and scope of the invention.

We claim:

1. An intersubband light emitter comprising:
   a core region including a multiplicity of repeat units, each repeat unit including a unipolar radiative transition (RT) region and a relaxation/injection (I/R) region adjacent thereto, characterized in that
   said at least one I/R region has a doping level that is at least 100 times lower than that of at least one other I/R region.

2. The emitter of claim 1, wherein said at least one I/R region has a sheet density that is at least 100 times lower than that of said at least one other I/R region.

3. The emitter of claim 2, wherein said at least one I/R region has a sheet density of about $10^8$–$10^9$ cm$^{-2}$ and said at least one other I/R region has a sheet density of about $10^{11}$–$10^{12}$ cm$^{-2}$.

4. The emitter of claim 1, wherein said at least one I/R region is undoped and said at least one other I/R region is doped to a level that is at least 100 times higher than that of said at least one I/R region.

5. The emitter of claim 1, wherein at least one of said RT regions is designed to emit optical radiation at a first center wavelength and at least one other RT region is designed to emit optical radiation at a second center wavelength different from said first wavelength.

6. A quantum cascade (QC) laser comprising:

a core region including a multiplicity of repeat units, each repeat unit including a unipolar radiative transition (RT) region and a relaxation/injection (I/R) region adjacent thereto, a pair of cladding regions bounding said core region, and electrodes for applying an electric field to said laser effective to cause said RT regions to generate stimulated emission of optical radiation, means forming an optical cavity resonator that includes said core region, characterized in that at least one I/R region is undoped and only a central section of at least one other I/R region is doped so that it has a sheet density that is at least 100 times greater than that of said at least one I/R region.

7. The laser of claim 6, wherein at least one of said RT regions is designed to lase at a first center wavelength and at least one other RT region is designed to lase at a second center wavelength different from said first wavelength.

8. The laser of claim 6, wherein said at least one I/R region and said at least one other I/R region are contiguous with the same RT region.

9. An intersubband light emitter comprising:

a core region including a multiplicity of repeat units, each repeat unit including a unipolar radiative transition (RT) region and a relaxation/injection (I/R) region adjacent thereto, characterized in that at least two I/R regions are contiguous with the same RT region and have doping levels that are different from one another.

10. The emitter of claim 9, wherein said at least two I/R regions have doping levels that are at least 100 times different from one another.

11. The emitter of claim 10, wherein said at least two I/R regions have sheet densities that are at least 100 times different from one another.

12. The emitter of claim 11, wherein one of said at least two I/R regions has a sheet density of about $10^8$–$10^9$ cm$^{-2}$ and the other of said at least two I/R regions has a sheet density of about $10^{11}$–$10^{12}$ cm$^{-2}$.

13. The emitter of claim 9, wherein one of said at least two I/R regions is undoped and the other of said at least two I/R regions is doped to a level that is at least 100 times higher than that of said one I/R region.

14. The emitter of claim 9, wherein at least one of said RT regions is designed to emit optical radiation at a first center wavelength and at least one other RT region is designed to emit optical radiation at a second center wavelength different from said first wavelength.

15. The emitter of claim 9 further including means for configuring said emitter to operate as a laser.

* * * * *